United States Patent [19]

Meyer et al.

[11] Patent Number: 5,888,190
[45] Date of Patent: Mar. 30, 1999

[54] HOLDING ARM SYSTEM

[75] Inventors: Michael Meyer, Obergrombach; Joachim Peuckert, Bönnigheim, both of Germany

[73] Assignee: Richard Wolf GmbH, Knittlinger, Germany

[21] Appl. No.: 884,075

[22] Filed: Jun. 27, 1997

[30] Foreign Application Priority Data

Jun. 27, 1996 [DE] Germany .......................... 196 25 729.8

[51] Int. Cl.⁶ .................................................. A61B 19/00
[52] U.S. Cl. ........................ 600/102; 248/278.1; 312/209
[58] Field of Search ..................................... 600/102, 104, 600/106, 107, 114; 248/278.1, 279.1, 276.1, 282.1, 283.1, 284.1, 288.51, 292.12; 312/209

[56] References Cited

U.S. PATENT DOCUMENTS

| | | | |
|---|---|---|---|
| 3,186,300 | 6/1965 | Littman | 600/102 |
| 4,784,463 | 11/1988 | Miyazaki | 600/102 |
| 5,184,601 | 2/1993 | Putman | 600/102 |
| 5,228,429 | 7/1993 | Hatano | 600/102 |
| 5,441,042 | 8/1995 | Putman | 600/102 |
| 5,540,649 | 7/1996 | Bonnell | 600/102 |
| 5,571,072 | 11/1996 | Kronner | 600/182 |

FOREIGN PATENT DOCUMENTS

| | | |
|---|---|---|
| 0 293 760 | 5/1988 | European Pat. Off. . |
| 27 00 661 | 8/1977 | Germany . |

*Primary Examiner*—Gene Mancene
*Assistant Examiner*—Ira Hatton
*Attorney, Agent, or Firm*—Cohen, Pontani, Lieberman & Pavane

[57] ABSTRACT

The invention relates to a holding arm system, particularly for holding surgical instruments in the region of an operation, with a holding arm incorporated into arm segments and into hinge joints connecting these. The holding arm at the proximal end is fastened to a rail which is guided in a horizontal position on the operating table. Each arm segment comprises straight-lined tube segments as outer sleeves and, in each arm tube, a shaft which is axially rotatable relative to the arm tube and which, with conical gearwheels on the end faces, engages into the shaft of the repective connecting arm segment. A fastening device is operable from a single arm segment and locks the whole holding arm by way of a braking device which engages at a defined location within the arm tube and by these means prevents the rotating of the shafts, connected with a positive fit, in the arm segments.

17 Claims, 10 Drawing Sheets

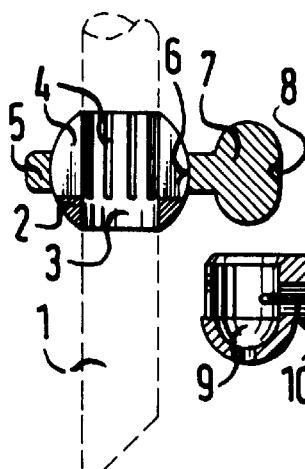
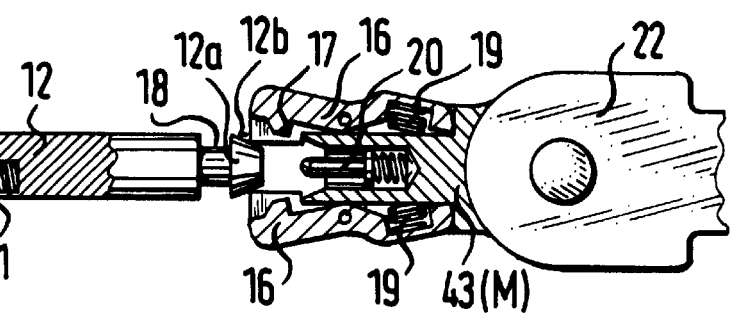
FIG. 2　　　FIG. 3　　　FIG. 4
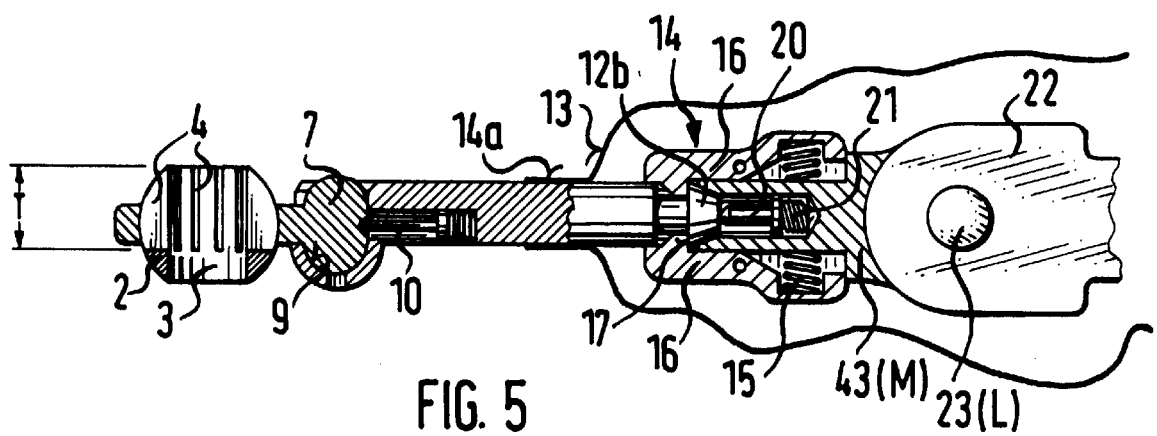
FIG. 5
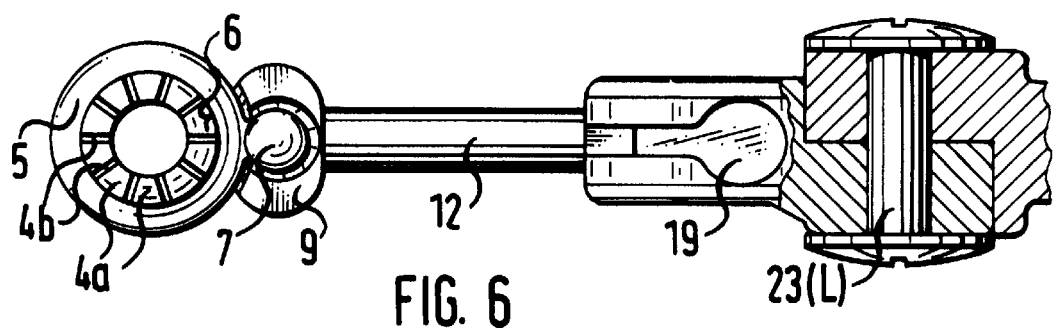
FIG. 6

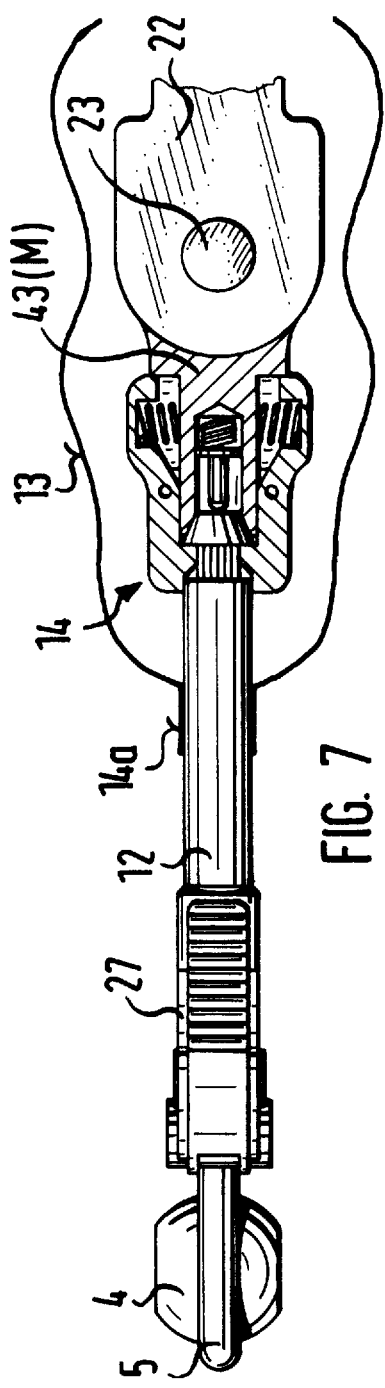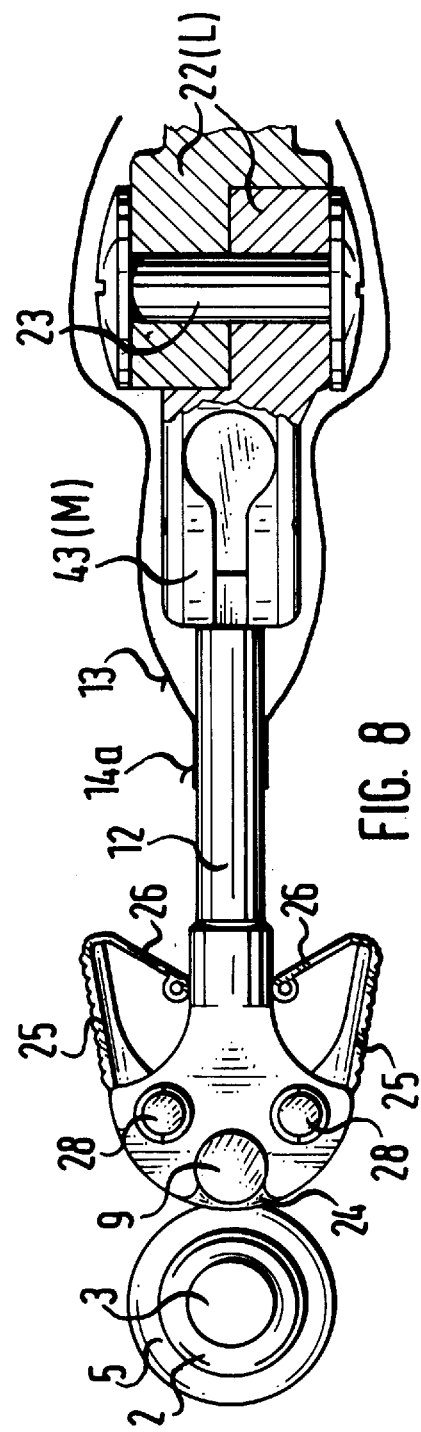

HOLDING ARM SYSTEM

BACKGROUND OF THE INVENTION

The invention relates to a holding arm system, in particular for holding medical instruments in the region of an operation.

Such a holding arm system is known from DE-A-2700661. For a holding arm system which is suitable for holding surgical instruments in the region of an operation, the following requirements are present:

- The holding arm system must have a locking, which can be operated from one point. With this locking, all those arm joints necessary for the change in position of the surgical instrument mounted at the distal end of the holding arm system must be easily fixable and releasable again.
- Each point in the operating region must be able to be reached with the instrument e.g. an endoscope, which depends on the respective operation technique. Further, the holding arm system must have a sufficient number of arm segments connected to one another in a jointed manner such that the instrument is movable over the operating table over a large as possible spacial angle and over a sufficiently large distance from the fastening point of the holding arm system.
- The higher the number of arms connected to one another in a jointed manner, the more important becomes the requirement that the locking is reliable and easily releasable for all arm segments.

The holding device for surgical auxiliary instruments described in the previously mentioned DE-A-2700661, for the locking of these instruments, comprises between an end effector interface and a holding block, a two-armed joint stand having a middle pivot joint. This joint stand with its one side is coupled to the end effector interface via a ball joint and on the other side is coupled via a further ball joint to an extension arm, which, relative to the holding block, can be tightened thereto at any position of height or rotation. The joint stand is formed tubular, and in the inside of this tube there is mounted an axially moving push rod which is pretensioned in the direction of a chuck lever by way of a spring. For its part, the chuck lever, for locking the connecting arm segment, operates conical sliding members which, when they are displaced by the chuck lever, displace the push rod in the direction of the connecting joint, so that a braking member attached here to the push rod effects the locking of this joint. This document also discloses a sterile hood which on application covers the whole holding arm system with the exception of the end effector interface and the applied instrument.

From EP-A-0293760 there is disclosed another holding arm system which is composed of several relatively freely moving arm segements in a first operational mode. The joints which connect these arm segments may be impinged upon by a small resistance force in a second mode of operation, so that a user can set the position of an instrument mounted at the distal end of the instrument to the desired setting whilst overcoming a small holding force, and it then remains at this setting.

In order to impinge the joints with this holding force, pressure tubes or hoses are guided through the arm segments and which undergo a pressure or vacuum by way of a pump. This means that this holding arm system is not securely lockable.

In view of the above state of the art it is the object of the invention to provide a holding arm system which can securely and rigidly hold a preadjusted instrument in its position without the effect of force, so that this locked position may only be deliberately changed by operating personnel.

This locking should be able to be operated from a single point, so that all arm joints of the holding arm system, necessary for the positional change at the distal end, may be easily lockable and releasable. The holding arm system must also be so designed that every point in the operation region can be reached by an instrument mounted on the distal end of the holding arm system.

Furthermore the system must guarantee that a suitable end effector interface formed as a quick change unit fulfils all the hygenic requirements of the respective operational technology. One requirement corresponds essentially to a separation into a sterile and semi-sterile section of the holding arm system.

BRIEF SUMMARY OF THE INVENTION

According to the invention the above object is achieved by a holding arm system, particularly for holding exchangeable surgical instruments in the region of an operation, with a proximal holding block serving the fastening of the holding arm system onto an immobile object and with a quick change unit at the distal side onto which the instrument may be applied and can be easily releasably fixed, wherein the holding block and the quick change unit are coupled by a number of arm segments which are connected by joints and which can be fastened in any position by a fastening device, wherein the individual arm segments of the holding arm system have outer shanks in the form of straight-lined tubes and wherein proceding from this, the holding arm system is characterized in that each joint is formed as a hinge joint, and that the fastening device comprises:

- an axially mounted shaft in each arm tube shank, said shaft in each case engaging, with engaging means on the end face side within the hinge joints, on the neighbouring shank, and
- on one of the arm segments, a single fastening handle which on operation mechanically engages into braking means and brings said braking means in frictional engagement with a braking surface fixed to an arm tube in such a manner that in cooperation with the connected shafts, the whole holding arm system is locked.

With the holding arm system according to the invention, in particular the following advantages are achieved:

- Since the joints of the holding arm system are formed as hinge joints, each joint in the locked condition may be locked with a high locking force by way of the shaft guided in the inside of the holding arm tube.
- Because the holding arm segments are formed tubular, the inside can be sealed against fluid and vapour and a sterile covering hose may be pulled from the end effector interface via the holding arm system up to the holding block.
- Since the fastening device comprises a handle formed on a single arm segment, with a simple hand grip, the whole holding arm system may be locked and released again.

Preferably, in each tube segment of the arms, the shafts end at the end face in conical gearwheels, which form positive fitting and reliable engaging means. The shaft in the fastening arm is rotated with a turning of the hand grip. In a braking hinge joint connecting to the fastening arm segment, there is mounted a sliding member which is displaceable in the axial direction of the braking hinge joint, said sliding member being displaced on turning of the grip. The displacement of the sliding element in the braking direction operates the braking means.

Furthermore the shaft in the fastening arm segment has eccentrically arranged cams at its end face. The sliding member is displaceable in the direction of the hinge axis of the connecting hinge joint, against the force of a pretensioned spring and the accompanying cam engages in a circumferential groove of the sliding member such that the cam in the eccentric position effects the displacement of the sliding member.

The sliding member comprises a central conical surface on its end face opposite the circumferential groove. A centrally mounted, axially displaceable reciprocating piston has an inversely formed conical surface, which sits on the conical surface of the sliding member. A displacement of the sliding member thus effects a corresponding axial displacement of the reciprocating piston which is transmitted to a truncated-cone-shaped friction disc. The friction disc then rests frictionally engaged with its outer annular surface on a complementarily formed braking surface of a caliper fixed to the arm tube, whilst the central shaft in the joint for its part is connected to the arm tube with a positive fit.

Furthermore, the quick change unit provided at the distal end of the holding arm system has an instrument receiving part and a connecting part which can be coupled to a connecting holding arm segment, wherein the instrument receiving part and the connecting part are connectable to one another in an easily releasable manner via a first quick coupler. Further, the connecting part and the connecting holding arm segment are connectable to one another in an easily releasable manner via a second quick coupler.

This distal end section, composed of the instrument receiving part and the connecting part, of the holding arm system is preferably designed for a one-off use and may be varied for differing instrument shank diameters. For a simple adaptation to the only slightly variable instrument shank diameter, the instrument receiving part further comprises a spherical body which has an outer surface with a spherical-shaped contour, a central bore for receiving the respective instrument shank, and in its spherical body, longitudinal slits arranged uniformly radially about the central bore, so that the spherical body is divided into a multitude of individual elastically connected ball segments and encloses the instrument shank in the central bore with a given pretension. Furthermore the outer surface of the spherical body is surrounded by a housing ring, which so rests on this spherical-shaped outer surface with a small frictional force, but slidably movable, that the spherical body with the interspersed instrument shank, is pivotable within a certain angular space.

Usefully, a first part of the first quick coupler is mounted to the housing ring surrounding the spherical body, this first coupler having the form of a short cylinder rounded at both its end faces. On the connecting part there is provided a second part of the first quick coupler which forms a hollow cylindrical coupling sleeve adapted to the form of the cylindrical part. An axially mounted, spring pretensioned securing pin of the second part of the first quick coupler engages, in the coupled condition of the first quick coupler, into a recess in the casing of the cylinder part, so that the first quick coupler holds the cylinder part rigidly, but easily releasably with finger pressure. At the end, facing the proximal side, of the cylindrically formed connecting part a cone with an annular shoulder is formed, which is a first part of the second quick coupler. Two spring loaded jaws are formed on the connecting arm segment of the holding arm system, these being a second part of the second quick coupler. In the coupled condition of the second quick coupler, lugs which are formed on the jaws, engage resiliently behind the annular shoulder of the first part of the second quick coupler. These lugs may be quickly released in that a slight pressure in exerted on the jaws so that the annular shoulder is released from the lugs.

Furthermore there is proposed a holding arm system according to the invention which comprises:

a holding arm sectioned into arm segments and joints connecting these arm segments, a holding block mounted to the proximal end of the holding arm for fastening the holding arm onto a stationary object, wherein the arm segments comprise, straight-lined tube segments as external shanks, a shaft which is axially mounted in each arm tube, rotatable relative to the arm tube and which engages, with conical gearwheels on the end faces, into the shaft of the respective connecting arm segment with a positive fit, wherein the joints in each case are formed as hinge joints each provided with a pivoting region, and wherein a fastening device can be operated from a single arm segment for locking the holding arm and which by way of a braking device locks a given shaft with respect to the assigned arm tube, so that due to the positive fit connection of the shafts the whole holding arm is locked.

Other objects and features of the present invention will become apparent from the following detailed description considered in conjunction with the accompanying drawings. It is to be understood, however, designed solely for purposes of illustration and not as a definition of the limits of the invention, for which reference should be made to the appended claims.

BRIEF DESCRIPTION OF THE SEVERAL VIEWS OF THE DRAWING

The invention is hereinafter described in more detail by way of the embodiment examples shown in the drawings. These show.

DETAILED DESCRIPTION OF THE INVENTION

Figure 1A:
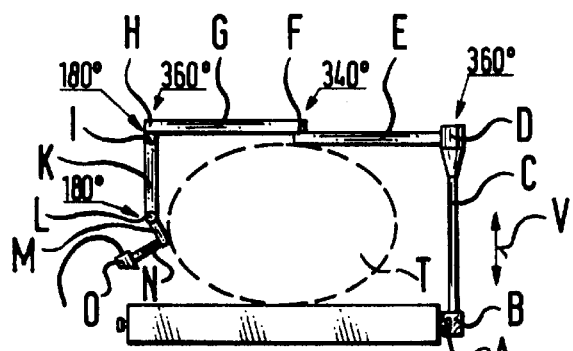
FIG. 1a a side elavation of a holding arm system according to the invention in a first position at the operation site, FIG. 1b a plan view of the holding arm system according to FIG. 1a with a different position shown dashed, FIG. 1c a side elevation of the holding arm system according to FIG. 1a, wherein the holding arm system assumes a different position to that in FIG. 1a, FIG. 1d a plan view of the holding arm system according to FIG. 1c with a different position shown dashed, FIG. 2 in section, the spherical receiver of the quick change unit, FIGS. 3 and 4 shown partly in section, the connecting part and the second quick coupler in the decoupled condition, FIG. 5 shown partly in section, the spherical receiver, the connecting part and the last arm segment on the distal side, in the decoupled condition, FIG. 6 a plan view of the distal end of the holding arm system according to FIG.5, FIGS. 7 and 8 an alternative embodiment form of the first quick coupler, in a lateral view and a plan view, FIGS. 9 and 10 in longitudinal sections, the second last arm segment on the distal side comprising the fastening grip, in a lateral view and a plan view, FIG. 11 longitudinally sectioned, two hinge joints connecting to the fastening arm segment and between which the braking device is arranged, FIG. 12 a part section through a further hinge joint, FIG. 13 a section through the head of the last proximal side arm segment, formed as a column, with the last hinge joint, FIGS. 14 and 15 a lateral view and section of the holding block attachable to a table rail, FIGS. 16a and 16b schematic representations showing the movability of the shank tube, inserted into the spherical receiver, of an instrument, e.g. an endoscope and FIGS. 17a to 17c an alternative to the spherical receiver shown in FIGS. 2 to 5.

Firstly by way of FIGS. 1a to 1d, the external construction of an embodiment form of the holding arm system according to the invention and its movability in the operating region is shown. FIG. 1a shows in a lateral view an embodiment form of the holding arm system according to the invention, which can be displaced with a holding block B on a longitudinal rail A on one side of an essentially horizontal table. With the holding block B, the whole holding arm system may be displaced horizontally on the rail over the whole length of the operating table. A body or torso T lying on the table is schematically illustrated with an outline.

The holding arm system shown in FIG. 1a is composed of, proceeding from the holding block B, a first arm segment C which is formed as a vertical column which is vertically displaceable (arrow V) in the holding block B with locking positions. Provided on the vertical column C is a first hinge joint or bearing D which permits the pivoting of a second arm segment E, connected to it in the distal direction, about 360°.

A second hinge joint F connects to the second arm segment E and permits a horizontal pivoting of a connecting third arm segment G about 340° with respect to the second arm segment E. A combination of a third and fourth hinge joint H, I follws the third arm segment G. The pivoting axes of the third and fourth hinge joints H, I are perpendiciular to one another. In this way the connecting forth arm segment K is horizontally pivotable about 340° and vertically pivotable about 180° with respect to the third arm segment G. The fourth arm segment K forms the fastening arm explained later. A fifth hinge joint L connecting to the fourth arm segment K allows the pivoting of the quick change unit N in a vertical plane about 180° with respect to the fourth arm segment K. The quick change unit N may also be considered as a sixth arm segment. On the quick change unit there is an instrument O e.g. an endoscope, with its shank inserted into a spherical receiver which is described later.

Figure 1C:
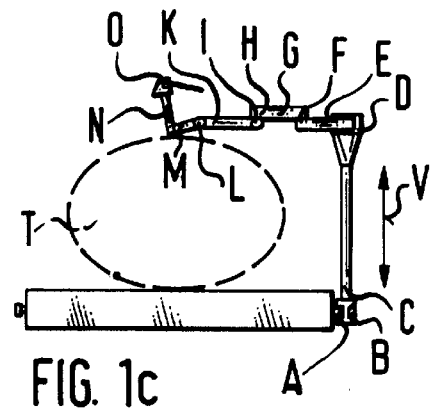
Figure 1B:
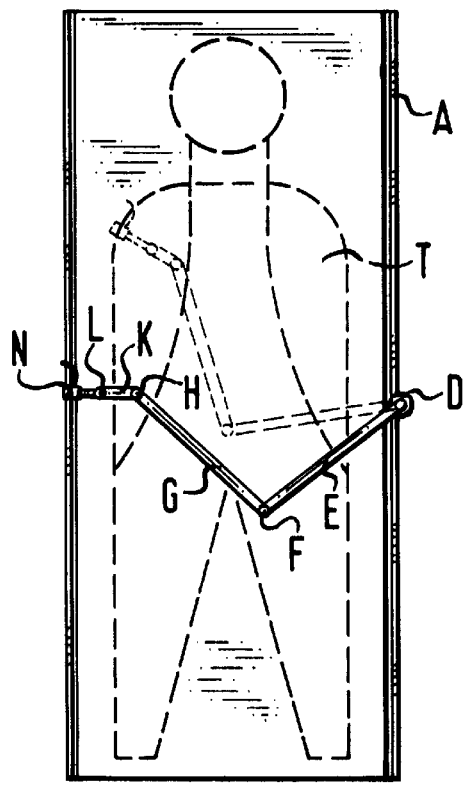

FIG. 1b shows a plan view of the previously explained holding arm system shown in FIG. 1a in a lateral view, wherein the position shown in FIG. 1a is shown in full lines and an alternative position is shown in dashed lines.

Figure 1D:
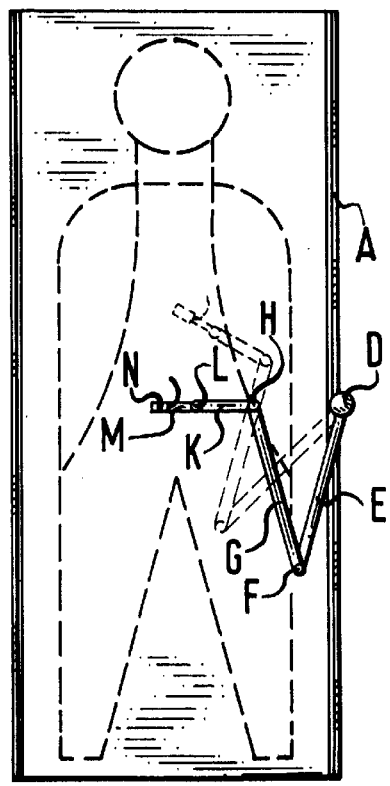

FIG. 1c shows a lateral view of an alternative position of the exact embodiment of the holding arm system according to FIG. 1a, wherein this is shown more clearly in the plan view shown in FIG. 1d. This also shows two alternative positions of the holding arm system, for the one part the position shown in FIG. 1c in full lines and for the other, the other position of the holding arm system in dashed lines. It is clear that the positions of the holding arm system according to the invention shown in FIGS. 1a to 1d are only examples and that without further ado, many other positions may be set and locked.

As will be later explained the individual arm segments are formed as straight-lined tube shanks. A sterilized covering hose indicated in FIG. 5 and the later explained FIGS. 7 and 8 may be easily pulled from the quick change unit N to the holding block B via all arm segments and joints. The whole holding arm system may be steam sterilized and prepared by machine. Moreover the whole holding arm system in an emergency situation can be dismantled from the operating table quickly or pivoted away from the operating table. Hereinafter by way of FIGS. 2 to 8 several embodiment forms of a quick change unit formed as an end effector holder are described.

FIG. 2 shows a spherical body, the dimensions of which are directed to the outer diameter of an instrument shank 1 to be inserted. For this, the spherical body 2 comprises a central bore 3 and longitudinal slits 4 radially surrounding this bore 3. By way of these slits the spherical body 2 is divided into a multitude of individual ball segments 4a (see also FIG. 6). The shank 1 of a surgical instrument, e.g. an endoscope shank, is held in the spherical body 2 in that the central bore 3 or the ball segments 4a surround the shank 1 of the instrument 1 with a given pretension. Due to the uniformly arranged longitudinal slits 4 and due to their depth T (see FIG. 5), an elastic deviation of the ball segments 4a radial to the direction of the axis of the instrument shank is made possible.

Due to an exact mutual dimensioning of the measurement of the diameter of the spherical body 2, of the diameter of the instrument shank, of the breadth and depth of the slits 4 and of a recess 6 in the distal region of the quick change unit, a given pretensioning of the ball segments 4a radial to the axial direction of the instrument shank 1 is achieved, which has such a magnitude that pushing the instrument shank in the bore 3 of the spherical receiver 2 is basically possible, and any unintentional adjustment or even the falling out of the instrument from the spherical body 2 is securely avoided.

Figure 16B:
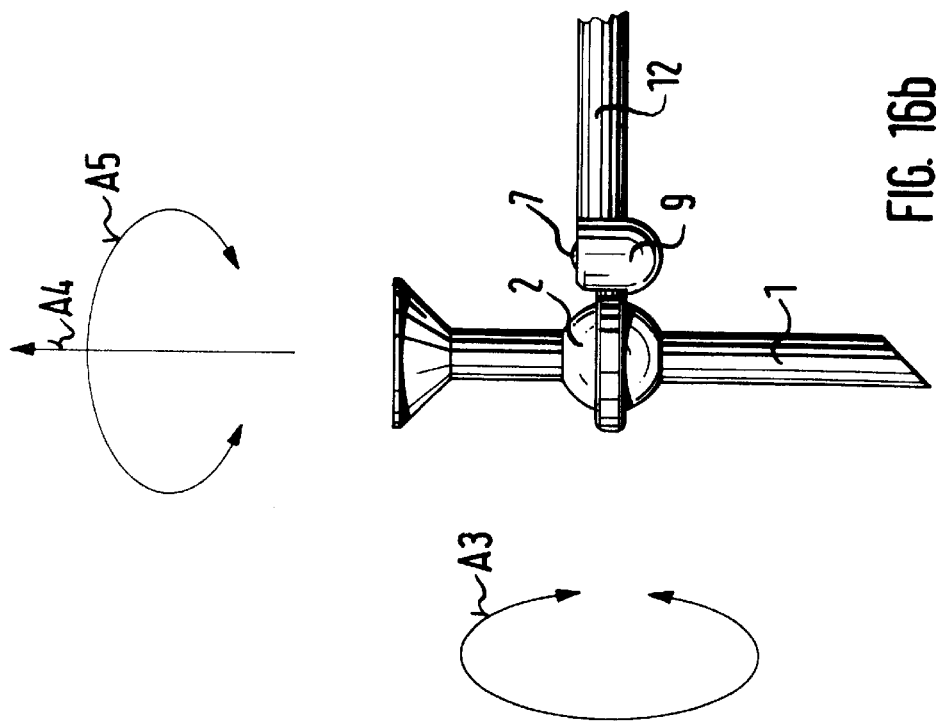
Figure 16A:
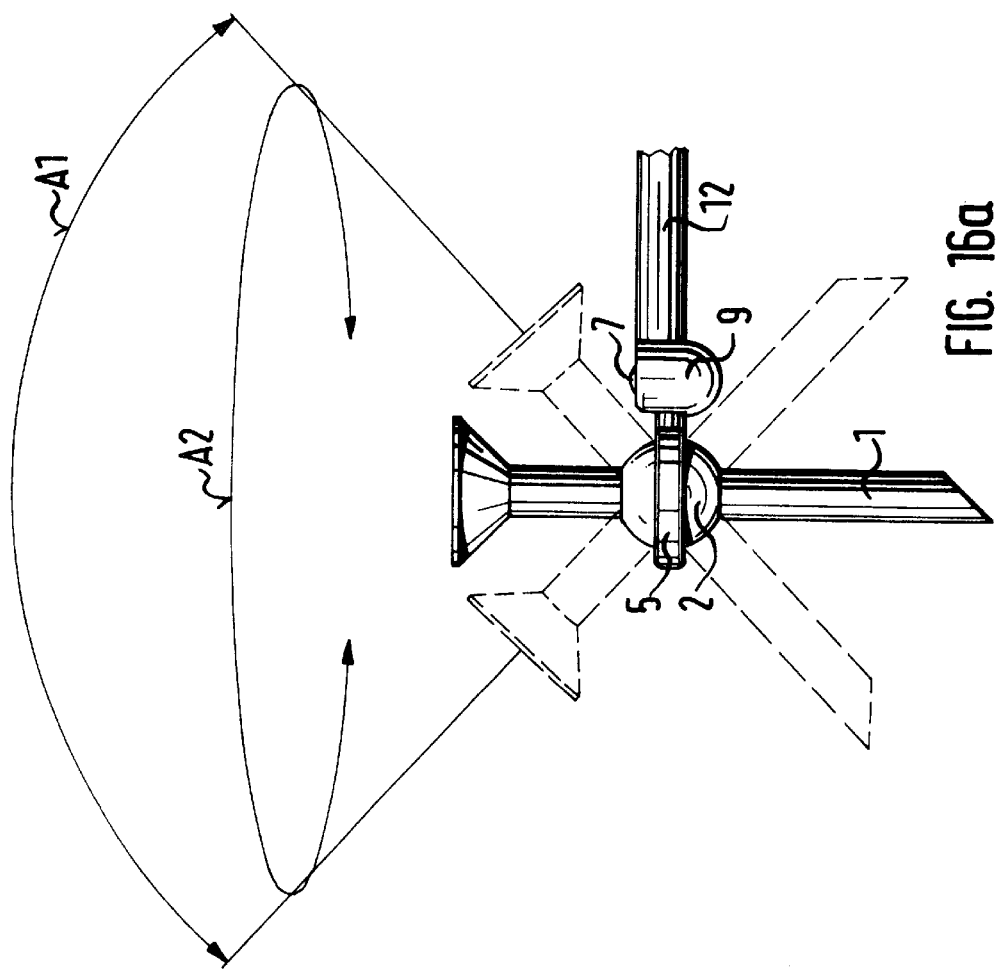

The spherically-shaped outer surface of the spherical body is surrounded by a housing ring 5 which so rests against the spherical-shaped outer contour in a sliding manner, that the spherical body 2 with the instrument may be pivoted within a given angular space indicated in FIG. 16a (see arrows A1 and A2 in FIG. 16). Further, the instrument shank 1 with the spherical body 2 may be rotated (arrow A4 in FIG. 16b). The whole quick change unit for its part, may be rotated in the direction of the arrow A3 indicated in FIG. 16b, as will be described later. Due to these pivoting and rotating possibilities of the instrument on and in the quick change unit, there results, additionally to the degrees of freedom of the holding arm system described above by way of FIGS. 1a to 1d, an even larger extension of the room for movement of the instrument held at the distal end of the holding arm system.

For a further explanation of the quick change unit and the first and second quick coupler mounted thereon, the FIGS. 2 to 8 are again referred to. On the housing ring 5 there is formed a cylinder body 7 which has rounded end faces on both sides and a recess 8 in its surface. On the opposite side, complementary to the cylinder body 7, a receiving sleeve 9 is formed on the connecting part 12. Further, a securing pin 10, pretensioned with a spring 11, is axially displaceably mounted in the connecting part 12 in the axial direction. This securing pin 10 prevents the instrument receiver from unintentionally releasing from the connecting part 12 in the coupled condition.

FIG. 5 shows the coupled together parts of the first quick coupler. A second quick coupler 14 is arranged at the proximal end of the cylindrically formed connecting part 12, with which the connecting part 12 can be quickly releasably connected to the last holding arm segment 43 on the distal side (M in FIG. 1a). The second quick coupler 14 comprises, on the side of the connecting part 12, a coaxial cone 12a, an behind this, an annular groove 18 formed on the cylindrical connecting part 12, so that an annular shoulder 12b is formed behind the cone 12a. On the side of the last arm segment 43, a conical receiver is mounted which comprises two jaws 16 each pretensioned with a compression spring 15, these jaws each comprising a lug 17 at their distal ends.

For a quick releasable connection between the connecting part 12 and the conical receiver it is necessary only to introduce the connecting part 12 under a slight pressure, with its end facing the cone 12a, into the conical receiver until both lugs 17 resiliently latch into the annular groove 18. An axially mounted pin 20 which is pushed by a spring 21 against the end face of the coupling cone 12a, effects the bearing of the annular shoulder 12b on both lugs 17. For releasing the coupling part 12 it is merely required that a pressure force is applied, against the springs 15, to finger rests 19 formed on the outer side of the jaws 16. In this way both the jaws 16 with their lugs 17 are pivoted radially outwards as is represented in FIG. 4. FIG. 5 shows the coupled condition of the second quick coupler, wherein the pin 20 pushes against the end face surface of the cone 12a by way of the spring 21.

As already previously mentioned (see arrow A3 in FIG. 16b) the connecting part 12 may be rotated in the second quick coupler. Moreover the conical receiver may be pivoted about the axis 23 which distally forms the last hinge joint (cf. L in FIG. 1a), this being so far until the finger rests 19 hit the holding arm 22. On the connecting piece 12 is fastened the covering hose 13 which is pulled over the whole holding arm system from the holding block, e.g by way of an adhesive tape 14a, as is shown in FIG. 5. The sterile unit, composed of a connecting piece 12 and the covering hose 13 shown in FIG. 5, in use is connected to the holding arm, and then the covering hose is proximally turned up, so that with the complete covering of the holding arm, any transmission of bacteria to the instrument part on the distal side is avoided.

The distal instrument part, comprising an endoscopic instrument 1 and the instrument receiver 2–8, for the purpose of exchanging the instrument, as has been described above, may be easily released from the connecting part 12 with the first quick coupler and exchanged for another instrument part. In addition, the instrument receiver 2–8 is preferably designed for one-off use. Since the endoscopic instrument 1 to be exchanged and the instrument receiver 2–8 are also sterilized before application, any transmission of bacteria can be ruled out.

Figure 17A:
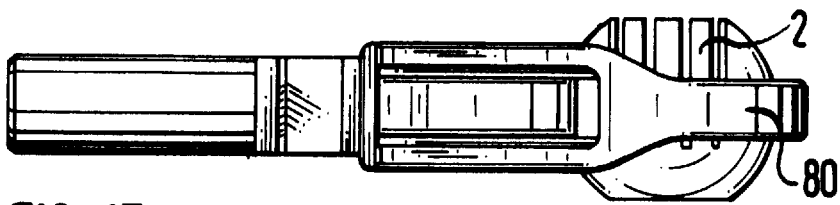
Figure 17B:
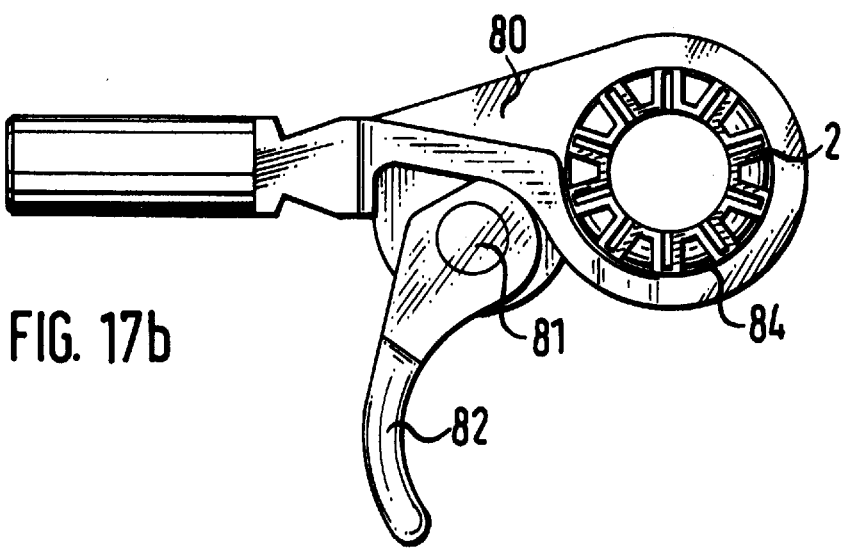
Figure 17C:
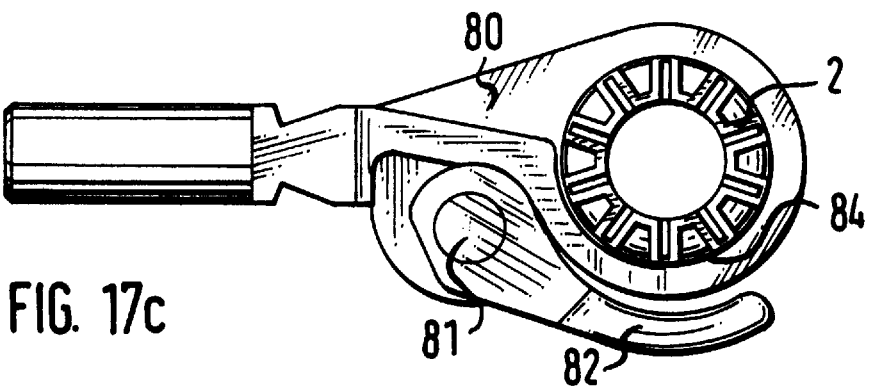

An alternative embodiment form of the instrument receiver of the quick change unit is shown in FIGS. 17a, b and c. The spherical body 2 may then be identical to that shown in FIGS. 17a, b and c. The spherical receiver 80 shown in FIGS. 17a, b and c has an adjustable outer ring 84 with which the required pretensioning on the spherical body 2 may be set. FIGS. 17b and c show how the pretensioning is transmitted via an eccentric 81 by way of a tension lever 82 on the outer ring 84 of the spherical receiver. The outer ring 84 is pulled together on tensioning the tension lever 82 by way of the eccentric effect of the eccentric 81, by which means the pretensioning on the spherical body is increased. There are also other possibilities for the adjustment and shaping of the external ring 84. For example instead of the tension lever with the eccentric, a tension screw, a conical thread, a toothing, an oblique plane with a wedge, tension sleeves and tension bands may be employed.

FIGS. 7 and 8 show an alternative embodiment form of the first quick coupler between the instrument receiver 2–8, which is identical with that shown in FIGS. 2, 5 and 6, and the connecting part 12. With regard to the embodiment form according to FIGS. 3, 5 and 6, the embodiment form shown in FIGS. 7 and 8 differs in that the cylindrical coupling part 7 formed on the instrument receiver, in the coupled condition, is surrounded with a positive fit by forceps type clamping jaws 24 which are operated by two handles 25. Further, the clamping jaws 24 are pivotably mounted on two parallel axes 28. On the handles 25 there are provided spring elements 26 which on the one hand engage on the handles 25 and on the other on the housing 27 of the first quick coupler. The proximal end of this alternative embodiment example, i.e. the second quick coupler and the hinge joint of the connecting arm segment 43, are identical to the embodiment form shown in FIGS. 3 to 6.

Figure 9:
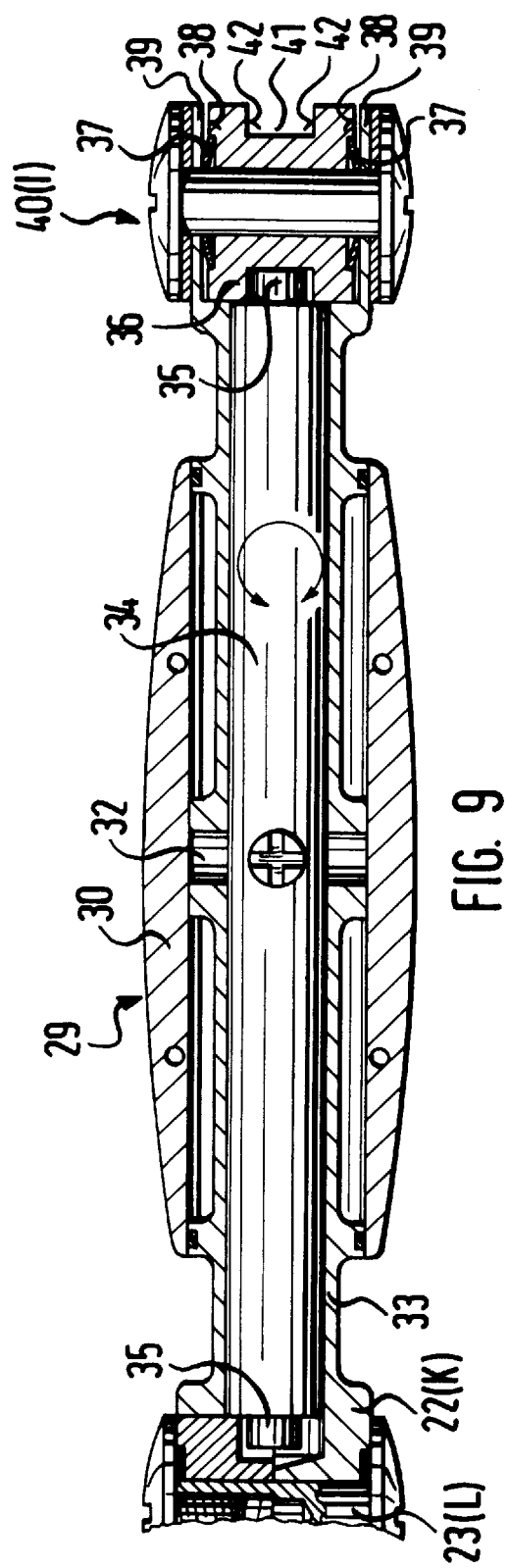
Figure 10:
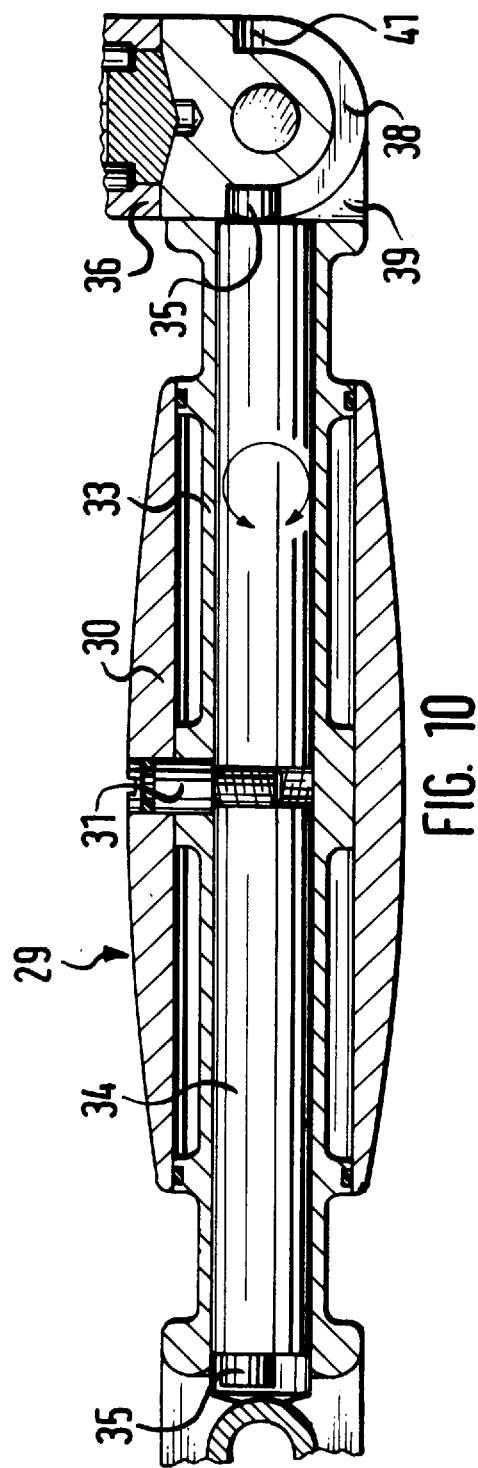

The FIGS. 9 and 10 show respectively from the side and from above, from the distal end of the holding arm system, the second arm segment 29 (K in FIG. 1a) which connects to the first arm segment 43 and the first hinge joint 22, 23 (L in FIG. 1a). This second arm segment 29 comprises a tubular shank 33, a shaft 34 which is rotatably movable and axially mounted therein and around the shank 33, a slightly barrel-shaped handle 30 which is rotationaly movable about the longitudinal axis and with which the holding arm may be locked at any position, so that the chosen position of the instrument up to the desired change in position is fixed against any unintentional adjustment.

The locking of the holding arm in the respective chosen position, or the releasing of the locking is effected by rotating the hand grip 30 (e.g. about approximately 90°), wherein this rotational movement is transmitted onto the shaft 34 rotatably mounted in the holding arm tube 33 via a driver 31 guided in a groove 32. At both end faces of the shaft 34 there are located eccentrically arranged cams 35. One of the cams 35, on rotation of the shaft 34 about its longitudinal axis, presses against one of two flanks 42 of a groove 41 in a sliding member 36, and by this effects a lateral displacement of the sliding member in the direction of the joint axis of the hinge joint 40 connecting to the holding arm segment 29.

The sliding member 36 is spring loaded by way of two plate springs 37 such that after turning back the hand grip 30, it automatically returns to the middle position. Due to the axial displacement of the sliding member 36, a frictional engagment between the end face 38 of the sliding member 36 and the inner side 39, facing this end face, of the hinge joint 40 is effected. This frictional engagement achieved by the contacting of both the surfaces 38, 39 may alternatively be increased in that the surfaces meeting one another may for example be provided with serrations such that these engage into one another with a positive fit.

Practically it has been shown that with merely the mentioned frictional engagement between the surfaces 38, 39, the whole holding arm system cannot always be sufficiently locked and that with the alternative application of serrations of both surfaces engaging into one another with a positive fit the adjustment or locking may only be possible in quite course angular steps.

For this reason the displacement of the sliding member 36, effected by turning the hand grip 30, should be transmitted to the fastening and braking device hereinafter described by way of FIG. 11.

Figure 11:
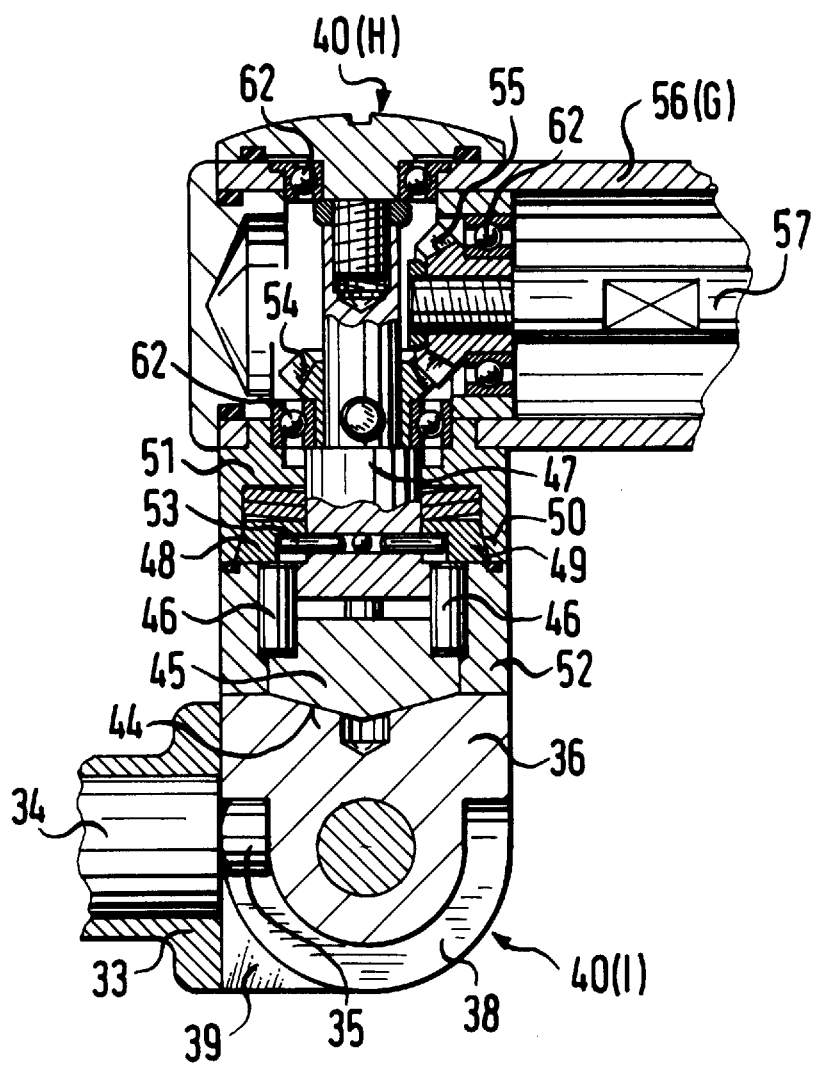

This FIG. 11 shows two combined hinge joints 40 which are perpendicular to one another in their pivoting direction. These hinge joints 40 correspond to those joints indicated in FIG. 1a with the letters I and H. It is already clear from FIG. 10 that the sliding member 36 has a centric conical recess 44 on its end face opposite to the circumferential groove 41. FIG. 11 shows that a reciprocating piston 45 is seated on the conical recess 44. The reciprocating piston 45 is axially mounted by four bolts 46 uniformly spaced in the circumferential direction which for their part engage into part cylindrical recesses, adapted to the bolt diameters, in the hinge housing. In this manner a displacement of the sliding member 36 is transmitted via the reciprocating piston 45 in the axial direction onto the four bolts and then onto a friction disc 48 arranged on the other side of the bolts. This friction disc then comes with its outer annular surface 49 into frictional engagement with a complementarily formed annular surface 50 of a caliper 51.

In the unbraked condition by way of the centrically arranged spring members it is effected that the outer, conical annular surface of the friction disc 48 is moved away by the complementarily formed annular surface 50 of the caliper 51, so that the lower part of the hinge joint 40 shown in FIG. 11 may rotate freely, in the axial direction of the shaft 47 mounted in this hinge joint, with respect to the upper part of the hinge joint 40.

In the upper part of the hinge joint 40, the shaft 57 is rigidly connected to the conical wheel 54 which is engaged with a positive fit with a complementarily formed conical wheel 55, which for its part is rigidly connected to a shaft 57 which is centrically and axially rotatably mounted in the connnecting arm segment 56.

In the braked condition the conical wheel 55 of the connecting arm segment 56 which is engaged with the conical wheel 54, is blocked against rotation because the shaft 47 is connected to the housing 52 of the hinge joint with a positive fit via bolts 46 and also, with the pins 53, a rotation of the friction disc 48 about the shaft 47 is prevented. Because of this then all shafts and joints, of the holding arm system, connected to one another by conical wheels on the end faces are locked. These include the arm segments 56 and 58 connecting to the hinge joint 40 (G and E in FIG. 1a) and the hinge joints connecting these segments (F and D in FIG. 1a). Only on overstepping a certain force can the arm segment E be rotated about the rotating hinge joint D on the column C (see FIG. 1a), since, as is shown in FIG. 13, the shaft 60 in the column 61 is connected to the conical wheel 54 located there by way of a sliding coupler 59.

In FIG. 11 ball bearings 62 are indicated which centrically and rotatably mount the shafts 47 and 57 directly behind the conical wheels 54, 55. A further ball bearing 62 is located on the upper end of the shaft 47.

Figure 12:
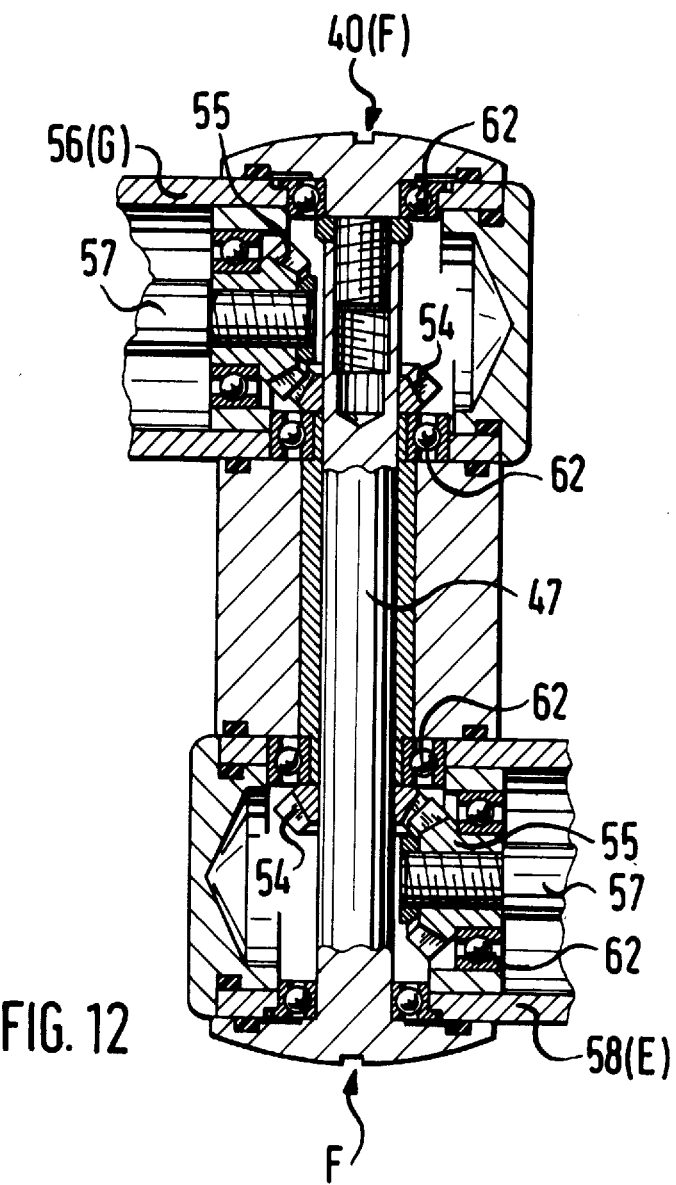

FIG. 12 shows the hinge joint F connecting to the arm segment 56 (G according to FIG. 1a), this joint connecting the arm segment (G) to the arm segment 58 (E). With its end face conical gearwheel 55, the shaft 57 mounted in the tube shank of the arm segment 56 is connected with a positive fit via a conical wheel 54, complementarily adapted to the gearwheel 55, to a shaft 47 mounted at right angles to the shaft 57. The shaft 47 for its part has a conical gearwheel 54 on its section which faces the neighbouring arm segment in the proximal direction. This conical gearwheel 54 is engaged with a positive fit with a complementary conical gearwheel 55, which is connected on the end face to the shaft 57 which lies at right angles to the shaft 47 and is centrally and rotatably movably mounted in the connecting arm segment E. For the mounting, ball bearings 62 are again employed.

Figure 13:
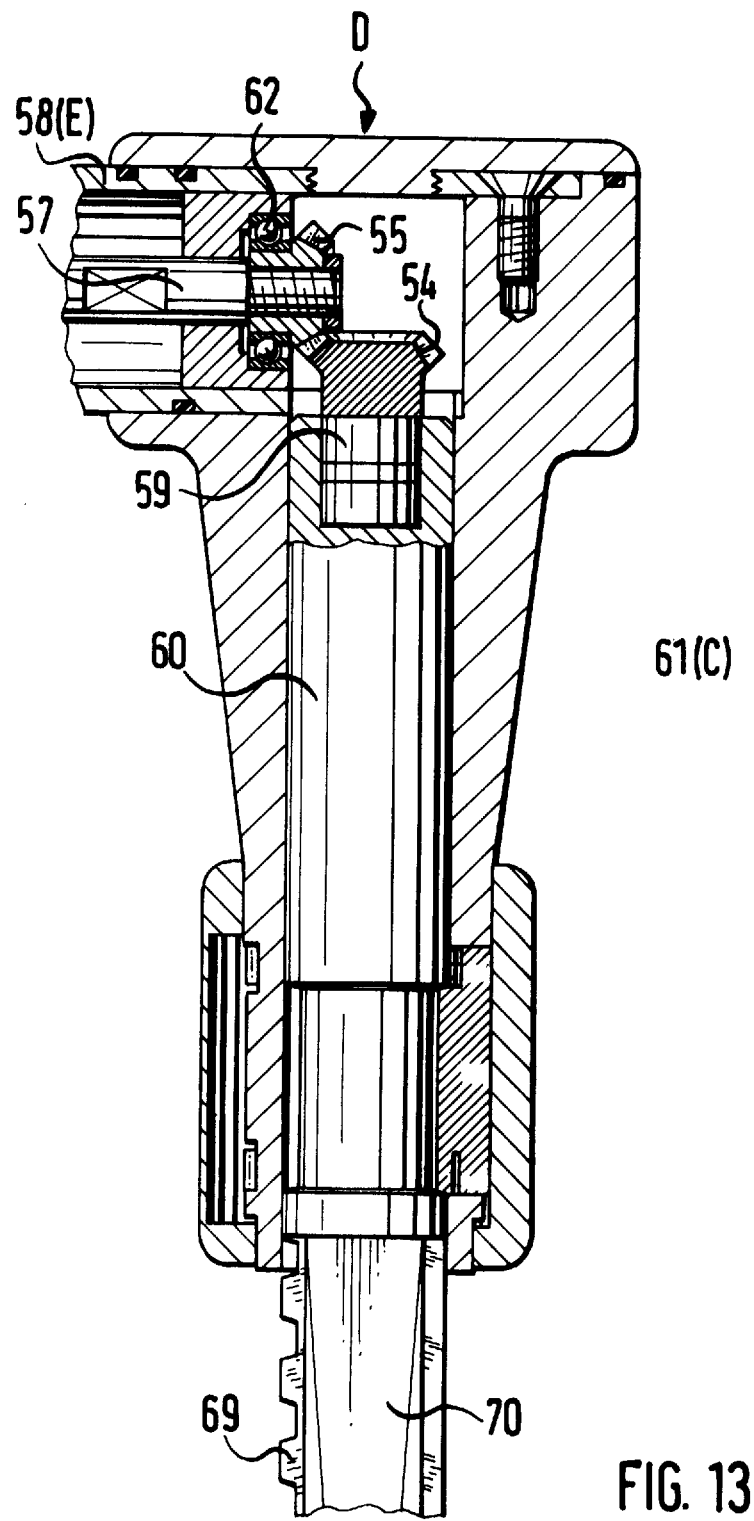

FIG. 13 shows the last hinge joint D on the proximal side, on the colum 61 (C in FIG. 1a). The shaft 57 which is mounted in the arm segment 58 (E) likewise comprises a conical gearwheel 55 on the end face which engages with a positive fit with a complementary conical gearwheel 54 which is connected to a shaft 60 in the column 61(C) via a sliding coupler 59. As has been previuosly mentioned, the sliding coupler 59 effects that also in the locked condition of the holding arm system, the arm segment 58 together with the arm segments connecting in the distal direction can be turned about the column 61 in a limited measure. In this way it is achieved that the whole holding arm system in the locked condition can be pivoted quickly away from the operating region with a forceful jolt.

Figure 15:
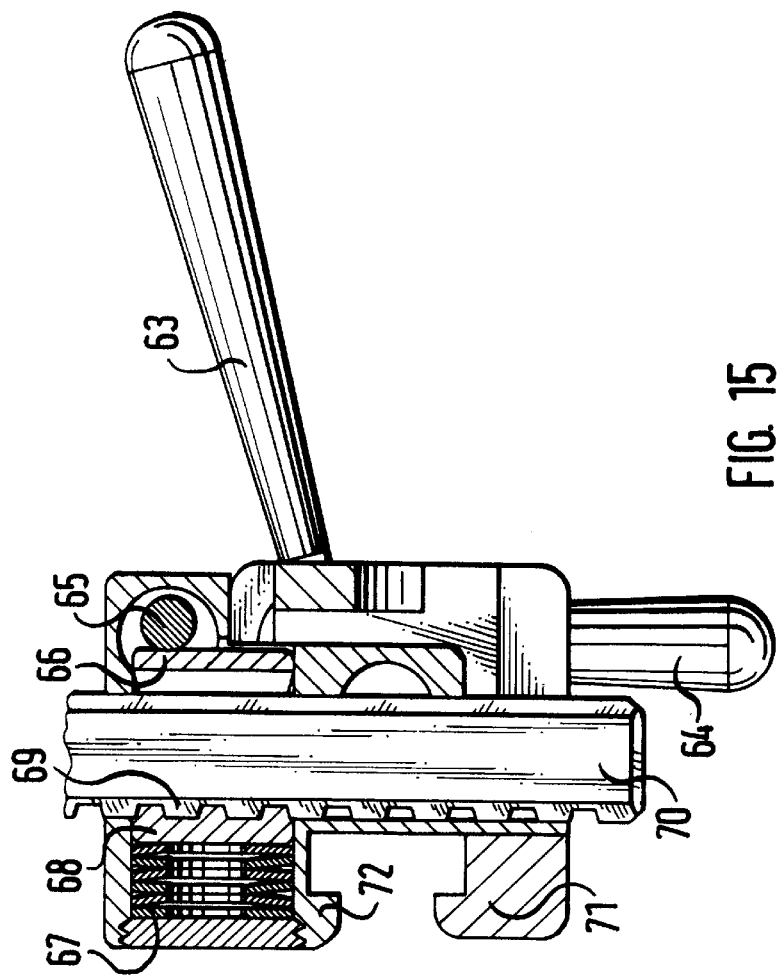
Figure 14:
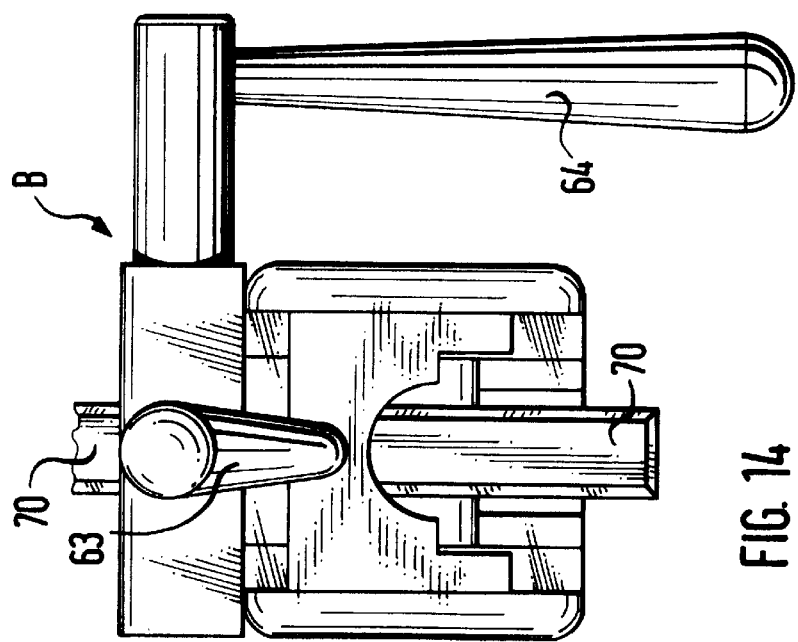

In FIGS. 14 and 15 the holding block holding the holding arm system on the table rail A, and a device for height adjustment of the holding arm system are shown. The height adjustment of the holding arm system may be carried out after pivoting a lever 64, by which means an eccentric member 65 displaces a latching device 66 to the left against the force of spring elements 67, so that a toothing 68 of the latching device, out of engagement, meets a corresponding toothing 69 of a rack 70. The rack 70 is rigidly connected to the column 61.

For tightening the holding arm system to the table rail a second lever 63 is firstly pivoted upwards, by which means a lower jaw 71 of the holding block carries out a movement opposite to the direction of movement of the second lever 63. When the holding arm system is located on the predetermined location on the table rail, the second lever arm 63 is pivoted downwardly by which means the tensioning jaws 71, 72 are tightened on the table rail.

It is still to be pointed out that the inside of the holding arm system is sealed to the outside by the usual sealing elements (e.g. O-rings) which are shown in the individual figures, so that steam sterilization of the holding arm system is possible without damp coming into the inside of the holding arm system.

Finally, it is noted that the instrument may also be introduced into the opening of the ball directly or with an intermediary of a sleeve. This then has the advantage that the spherical shape and in particular also the diameter of the central opening may be maintained, whilst differences of diameters when using differing instruments may be overcome using compensating sleeves or likewise. In this way one can avoid having to manufacture a multitude of balls with different openings for receiving the instruments and practically having these available on location. In particular the manufacture is of most importance, since in any case, compensating sleeves may be produced more simply than spherical receivers.

Thus, while there have shown and described and pointed out fundamental novel features of the invention as applied to a preferred embodiment thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. It is the intention, therefore, to be limited only as indicated by the scope of the claims appended hereto.

We claim:

1. A holding arm system for positioning and holding a medical instrument in a region of an operation, comprising:

a proximal holding means for fastening the holding arm system to an immobile. object;

a distal quick change means for receiving and releasably retaining the medical instrument;

a plurality of connected arm segments comprising outer tubular shanks, for coupling said proximal holding means and said distal quick change means and for and positioning said plurality of arm segments, said quick change means and the medical instrument at one of a plurality of positions in the region of the operation;

a plurality of joints for connecting at least a portion of said plurality of arm segments to one another, each joint of said plurality of joints being formed as a hinge joint with a predefined pivoting region; and fastening means, positioned within at least a portion of said plurality of arm segments, for releasably locking said plurality of arm segments at said one of said plurality of positions, said fastening means comprising:

an axially mounted shaft in each of said arm segment tubular shanks, each said shaft being axially rotable relative to its respective arm segment tubular shank, each of said shafts having a first end and a second end and having engaging means on at least one of said first and second ends and positioned within one of said joints, for engaging, with a positive fit, engaging means of at least one other shaft;

breaking means, positioned on a particular arm segment of said plurality of arm segments, for immobilizing said particular arm segment shaft, wherein when said particular shaft is immobilized when said plurality of arm segments is in a particular position of said plurality of positions, all of said shafts are immobilized due to positive engagement between said engagement means of said shafts, thereby locking said plurality of arm segments in said particular position; and fastening activation means, positioned on said particular arm segment, for selectively activating and deactivating said breaking means.

2. The holding arm system of claim 1, wherein:

said engagement means comprise conical gearwheels on all said shafts except for said particular shaft;

said fastening activation means comprises an essentially cylindrical handle grip rotably mounted about said particular arm segment, said handle grip engaging said particular shaft such that when said handle grip is rotated, said particular shaft is rotated within said particular arm segment tubular shank; and said particular arm segment is connected to a particular hinge joint, having a hinge axis, wherein said particular hinge joint comprises a sliding member having an end face and being displaceable in a direction of said hinge axis of said particular hinge joint, said sliding member being displaced when said handle grip is rotated, wherein said breaking means is activated by said displacement of said sliding means.

3. The holding arm system of claim 2, wherein:

said particular shaft comprises an eccentrically positioned cam at said first end;

said particular hinge joint comprises a first pretensioned spring for opposing said displacement of said sliding member in the direction of said hinge axis; and said sliding member comprising a circumferential groove positioned opposite to said end face, for engaging said cam such that when said handle grip is rotated said particular shaft rotates said cam causing said sliding member to be displaced.

4. The holding arm system of claim 3, wherein:

said sliding member further comprises a central first conical surface on said end face; and said particular hinge joint further comprises:

a joint housing having an inner caliper portion, said caliper portion having an inner annular surface;

a centrally positioned axially displaceable reciprocating piston, having a second conical surface that is formed inversely to said first conical surface for positive contact with said first conical surface;

a truncated cone-shaped friction disk comprising an outer annular surface for frictionally engaging said inner annular surface, said friction disk being connected to said reciprocating piston such that displacement of said sliding member axially displaces said reciprocating piston and said friction disk; and a central shaft positioned within said joint housing and connected to said joint housing via a positive fit, said central shaft having a proximal end, a distal end, and a conical braking gearwheel positioned at said proximal end for engaging a conical gearwheel of another of said shafts, such that when said sliding member is displaced by turning said handle grip, said friction disk positively engages said housing through said respective inner and outer annular surfaces thereby preventing rotation of said central shaft, locking said breaking gearwheel and said another gearwheel and thus locking all interconnected arm segments into their current position by preventing movement of the shafts disposed therein.

5. The holding arm system of claim 1, wherein said quick change means comprises:

instrument receiving means for receiving and releasably holding the medical instrument;

a connecting part, for connecting said instrument receiving means to a connecting arm segment, said connecting part having a proximal end and a distal end, and said connecting arm segment comprising an arm segment of said plurality of arm segments that is connected to only one other arm segment;

first releasable coupling means for releasably connecting said instrument receiving means to said connecting part; and second releasable coupling means for releasably connecting said connecting part to said connecting arm segment.

6. The holding arm system of claim 5, wherein said instrument receiving means comprises:

a spherical body having a spherically shaped outer surface;

a central bore in said spherical body for receiving the medical instrument;

a plurality of longitudinal slits arranged uniformly and radially within said spherical body and about said bore, such that said spherical body is partitioned into a plurality of elastically connected segments enclosing and releasably retaining the medical instrument in said bore with a predefined compressive force that must be manually overcome for removal of the medical instrument from said bore; and a housing ring surrounding and retaining said spherical body in a sliding manner, such that said spherical body with the medical instrument disposed in said bore therein is pivotable within said housing ring and within a predefined angular space.

7. The holding arm system of claim 6, wherein said first releasable coupling means comprises:

a first coupling part connected to said housing ring, said first coupling part comprising a substantially short cylinder body having an outer wall section facing said connecting part, a substantially rounded first end and a substantially rounded second end, and having a recess in said outer wall section; and a second coupling part, connected to said proximal end of said connecting part, said second coupling part comprising a hollow cylindrical sleeve sized and shaped to receive said cylinder body of said first coupling part, and a pretensioned securing pin for releasably engaging said recess when said cylinder body is inserted into said cylindrical sleeve.

8. The holding arm system of claim 5, wherein said connecting arm segment comprises an end face and wherein said second releasable coupling means comprises:

an axial cone disposed at said distal end of said connecting part;

an annular groove radially defined in said connecting part behind said axial cone;

a pair of jaws forming a conical receiving area in a closed position for receiving said axial cone, each of said jaws having an engaging end and being positioned on said end face of said connecting arm segment in confronting opposition to said distal end of said connecting part;

spring means connected to said jaws for radially pretensioning each said jaw into a closed position; and a lug positioned at said engaging end of each said jaw, oriented such that when said jaws are closed about said axial cone, said lugs are resiliently latched in said annular groove, wherein said releasable coupling means may be released by applying force against said spring means to release said jaws from engagement about said axial cone.

9. A system for holding an object in one of a plurality of positions, comprising:

a holding arm comprising a first, a second, a third, a fourth and a fifth arm segment, said arm segments being interconnected by a first, a second, a third, a fourth and a fifth joint, each said arm segment comprising a tubular shank and an inner shaft being rotable with respect to said tubular shank, each said shaft having at least one end face with a conical gearwheel, wherein said at least one conical gearwheel engages at least one other conical gearwheel of at least one other arm segment shaft to form a positive fit between all arm segment shafts, and wherein each said joint comprises a hinge joint with a predefined pivoting region;

a holding block connected to said first arm segment for fastening said holding arm to an immobile object; and locking means positioned on one of said arm segments for releasably locking one of said arm segment shafts to prevent said one arm segment shaft from rotation and thereby locking all other arm segment shafts positively connected by said gearwheels from rotation such that said holding arm is locked in a particular position of a plurality of positions.

10. The system of claim 9, wherein said holding block is horizontally displaceable and fastenable at one of a plurality of horizontal positions along said immobile object.

11. The system of claim 9, wherein said first arm segment comprises a vertical column movably connected to said holding block, said first arm segment being vertically displaceable with respect to said holding block.

12. The system of claim 9, wherein said second arm segment is connected to said first arm segment by said first joint and wherein said second arm segment is horizontally pivotable about 360 degrees with respect to said first arm segment.

13. The system of claim 9, wherein said third arm segment is connected to said second arm segment by said second joint and wherein said third arm segment is horizontally pivotable about 340 degrees with respect to said second arm segment.

14. The system of claim 9, wherein said fourth arm segment is connected to said third arm segment by a combination of said third joint and said fourth joint and wherein said fourth arm segment is horizontally pivotable about 340 degrees and vertically pivotable about 180 degrees with respect to said third arm segment.

15. The system of claim 9, wherein said fifth arm segment is connected to said fourth arm segment by said fifth joint and wherein said fourth arm segment is vertically pivotable about 180 degrees with respect to said fourth arm segment.

16. The system of claim 14, wherein said locking means is positioned on said fourth arm segment, said locking means comprising;

a locking device positioned in said combined third and fourth joint and connected to said fourth arm segment shaft, for releasably locking said other arm segment shafts; and a turning grip positioned about said fourth arm segment outer tubular shank and connected to said fourth arm segment shaft therein, such that when said turning grip is rotated, said fourth arm segment shaft is also rotated, wherein said locking device is activated and later deactivated by rotation of said fourth arm segment shaft.

17. The system of claim 9 wherein said fifth arm segment comprises a distal end, said system further comprising:

a releasable instrument receiving device for receiving and releasably retaining an instrument; and a pivotable quick coupling device for releasably connecting said instrument receiving device to said distal end of said fifth arm segment, such that said instrument receiving device with an inserted instrument may be easily pivoted about a predefined angular space relative to said fifth arm segment.

* * * * *